(12) United States Patent
Johnson et al.

(10) Patent No.: US 6,872,347 B2
(45) Date of Patent: Mar. 29, 2005

(54) EXOSKELETAL LEG PROSTHESIS AND METHOD FOR ALIGNMENT

(75) Inventors: Christopher L. Johnson, Plainwell, MI (US); Eric L. Robinson, Sterling Heights, MI (US); Michael J. Link, Chesterfield, MI (US)

(73) Assignee: College Park Industries, Inc., Fraser, MI (US)

( * ) Notice: Subject to any disclaimer, the term of this patent is extended or adjusted under 35 U.S.C. 154(b) by 0 days.

(21) Appl. No.: 10/747,326

(22) Filed: Dec. 29, 2003

(65) Prior Publication Data

US 2004/0140581 A1 Jul. 22, 2004

Related U.S. Application Data

(62) Division of application No. 09/970,203, filed on Oct. 4, 2001, now Pat. No. 6,692,533.
(60) Provisional application No. 60/237,859, filed on Oct. 4, 2000.

(51) Int. Cl.[7] .................................................. A61F 2/76
(52) U.S. Cl. .................................... 264/271.1; 623/901
(58) Field of Search ........................... 623/901, 33, 36, 623/38, 47, 50, 52, 53; 602/27; 264/271.1

(56) References Cited

U.S. PATENT DOCUMENTS

| | | |
|---|---|---|
| 3,940,804 A | 3/1976 | Benton et al. |
| 4,636,220 A | 1/1987 | Ziegelmeyer |
| 4,923,476 A * | 5/1990 | Cooper et al. ................. 623/38 |
| 5,425,781 A | 6/1995 | Allard et al. |
| 5,755,812 A | 5/1998 | Becker et al. |
| 5,913,902 A | 6/1999 | Geible |
| 5,993,488 A | 11/1999 | Phillips |
| 6,123,732 A | 9/2000 | Gramnas |
| 6,129,766 A | 10/2000 | Johnson et al. |
| 6,312,475 B1 | 11/2001 | Voisin |
| 6,497,028 B1 * | 12/2002 | Rothschild et al. ........... 29/416 |
| 6,692,533 B2 | 2/2004 | Johnson et al. |

FOREIGN PATENT DOCUMENTS

| | | | |
|---|---|---|---|
| DE | 2 101 254 | 7/1972 | |
| FR | 2 708 848 A1 * | 2/1995 | ............. A61F/2/62 |
| JP | 2000-139975 A | 5/2000 | |
| SU | 721094 | 3/1980 | |

\* cited by examiner

*Primary Examiner*—David H. Willse
(74) *Attorney, Agent, or Firm*—Howard & Howard

(57) ABSTRACT

An ankle block for a leg prosthesis comprising an insert having a body with an upper mounting surface and a bottom interface surface opposite from the upper mounting surface. The insert body defines a central coaxial hole therethrough. An over mold is formed about an exterior of the body and extends upwardly therefrom defining a central cavity above the insert and above the upper mounting surface.

2 Claims, 7 Drawing Sheets

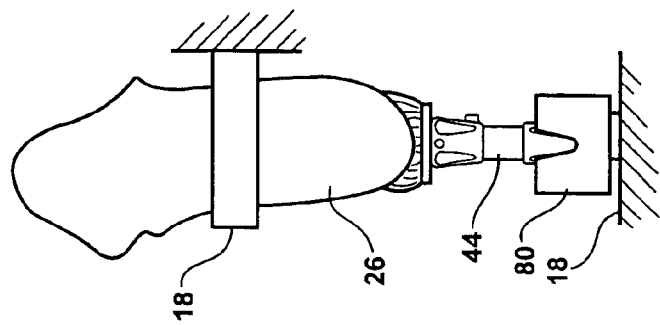
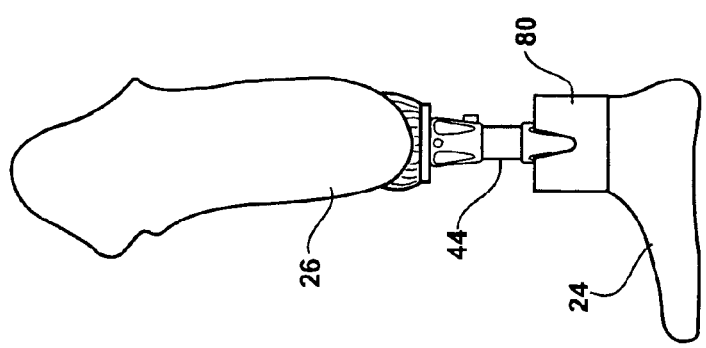
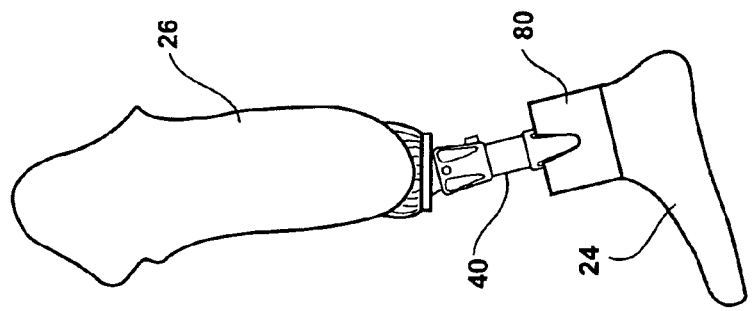
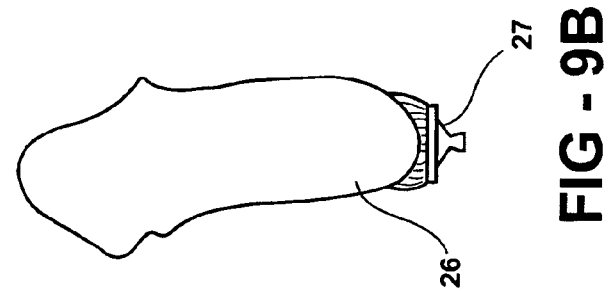
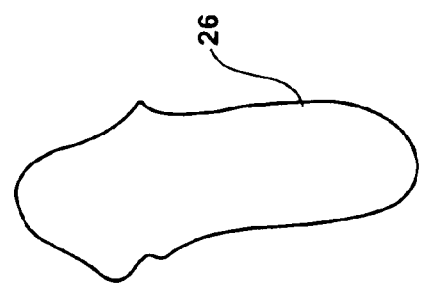

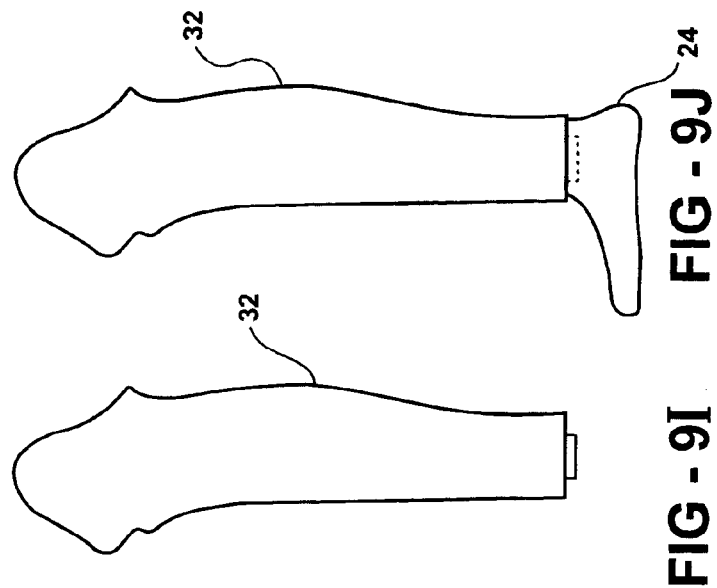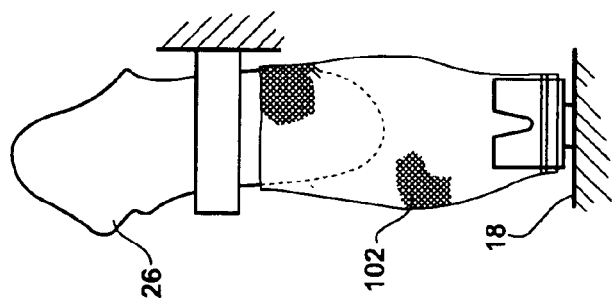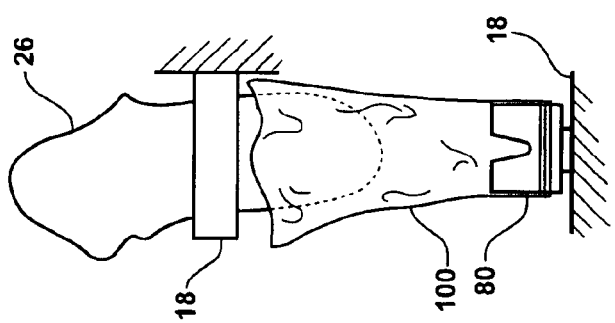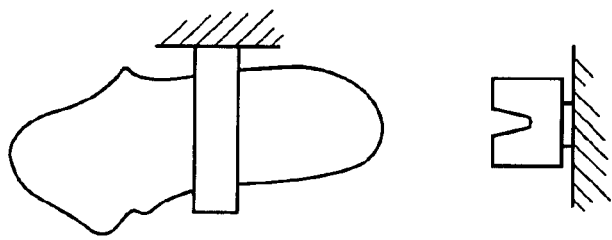

EXOSKELETAL LEG PROSTHESIS AND METHOD FOR ALIGNMENT

This application is a divisional of application Ser. No. 09/970,203, filed Oct. 4, 2001, now U.S. Pat. No. 6,692,533, which claims priority to provisional application 60/237,859 which was filed on Oct. 4, 2000.

BACKGROUND

The present invention relates to lower leg prostheses and methods of assembly and alignment of lower leg prostheses and more particularly to an improved apparatus and method of assembly and alignment.

Traditionally there are two types of lower leg prostheses, an external or exoskeletal apparatus and an internal or endoskeletal apparatus. The exoskeletal apparatus consists of a rigid leg component shaped in the appearance of the external human leg, attached to a foot. Traditionally, the leg component was constructed of solid wood, but now it is more commonly constructed of a resin or lightweight composite material formed around a solid structural foam interior. The composite laminate leg component is extremely lightweight, strong, and capable of supporting very heavy loads. The leg component is attached to the limb of a person through a socket. The leg component is attached to an artificial foot through a block in the ankle area. The ankle block is usually solid wood or structural foam and contains a fastening mechanism such as a bolt and nut fastener to attach the artificial foot and the ankle block is usually permanently attached to the leg portion through the laminate of the leg component.

The method of forming the exoskeletal leg apparatus and aligning the socket and foot for a particular patient traditionally involves an initial bench alignment based on the experience of the prosthetist constructing the apparatus. The alignment of the apparatus is extremely important to the effectiveness and comfort of the finished device. After the leg portion is cast and attached to the ankle block further alignment of this portion is impossible without cutting the cast portion and re-constructing it. The only adjustment easily made by the prosthetist after forming the exoskeletal leg is the minor adjustment of foot rotation made possible through the foot fastener. Thus, due primarily to the alignment difficulty, the modem trend has been away from the exoskeletal leg prosthesis toward a more adjustable endoskeletal leg.

The endoskeletal leg apparatus comprises a series of tubes, simulating the bones of the leg, connected via adjustable components to the artificial foot and covered by a cosmetic cover to look like a human leg. The endoskeletal components are traditionally lightweight metals interconnected with fasteners and adjustable components. The advantage of the endoskeletal leg is that all of the components remain adjustable and are easily maintained and replaced if necessary. The components have also been standardized by many manufacturers for easy interchangeability and modularity. The main advantage of the endoskeletal apparatus is the ability for the prosthetist to align the leg by adjusting the components after the leg is statically and dynamically loaded by the end user during a fit test process. The process includes attaching a completely assembled apparatus including a foot to a user and allowing the user to stand and walk on the leg to determine the proper alignment. During this process, minute adjustments are made perfecting the alignment of the leg resulting in a more comfortable and effective prosthesis. The disadvantage of the endoskeletal leg is its relative high cost, its weight, its complexity, its noise potential due to multiple interconnected metal components, its mechanical appearance, and its lower strength capabilities as compared to the exoskeletal apparatus.

Thus what is desired is an improved apparatus and method of constructing and aligning an exoskeletal leg prosthesis.

SUMMARY OF THE INVENTION

One aspect of the present invention is an ankle block for a leg prosthesis. The ankle block comprises an insert having a body with an upper mounting surface and a bottom interface surface opposite from the upper mounting surface. The insert body defines a central coaxial hole therethrough. An over mold is formed about an exterior of the body and extends upwardly therefrom defining a central cavity above the insert and above the upper mounting surface.

Another aspect of the present invention is a method of constructing an exoskeletal leg prosthesis. The method comprises the steps of forming a leg socket for receiving the leg of a user and affixing a temporary adapter to a bottom of the leg socket. An ankle block is attached to the top of a prosthetic wherein the ankle block includes an insert for attaching the block to the foot and an outer mold molded over the insert and having an upwardly extending portion defining a recess therein. A temporary adapter is affixed to an upper surface of the ankle block and an endoskeletal pylon system is attached to the adapters on the ankle block and the leg socket to create a temporary adjustable prosthetic leg. The endoskeletal pylon is adjusted to align the prosthetic foot with respect to the leg socket. After the prosthetic foot is aligned with the leg socket, the prosthetic foot is removed from the ankle block. The adjusted leg is retained in a fixture whereupon the endoskeletal pylon and temporary adapters are removed while maintaining the leg socket and ankle block in their adjusted alignment. A structural foam support is molded between the leg socket and the ankle block and then an outer structural shell is laminated to the combined leg socket, foam support, and ankle block. The prosthetic foot is then reattached to the ankle block.

Yet another aspect of the present invention is a method for constructing an exoskeletal prosthetic leg. The method comprises the steps of providing a leg socket and an ankle block affixed to a prosthetic foot. A temporary adjustable endoskeletal pylon is attached between the leg socket and the ankle block. The pylon is adjusted to dynamically align the prosthetic foot with respect to the leg socket. The pylon is adjusted in a dynamic fashion to align the prosthetic foot with respect to the leg socket. The aligned prosthetic leg is then clamped in a fixture and the temporary endoskeletal pylon is removed while maintaining the adjusted alignment of the leg socket with respect to the ankle block. An inner foam core is constructed between the leg socket and the ankle block and a laminated shell is then applied to an exterior of the combined leg socket, foam core, and ankle block.

These and other advantages of the invention will be further understood and appreciated by those skilled in the art by reference to the following written specification, claims and appended drawings.

BRIEF DESCRIPTION OF THE DRAWINGS

FIGS. 9A-J is a stepped sequence of the construction of an exoskeletal leg embodying the present invention.

DETAILED DESCRIPTION OF THE PREFERRED EMBODIMENT

Figure 2:
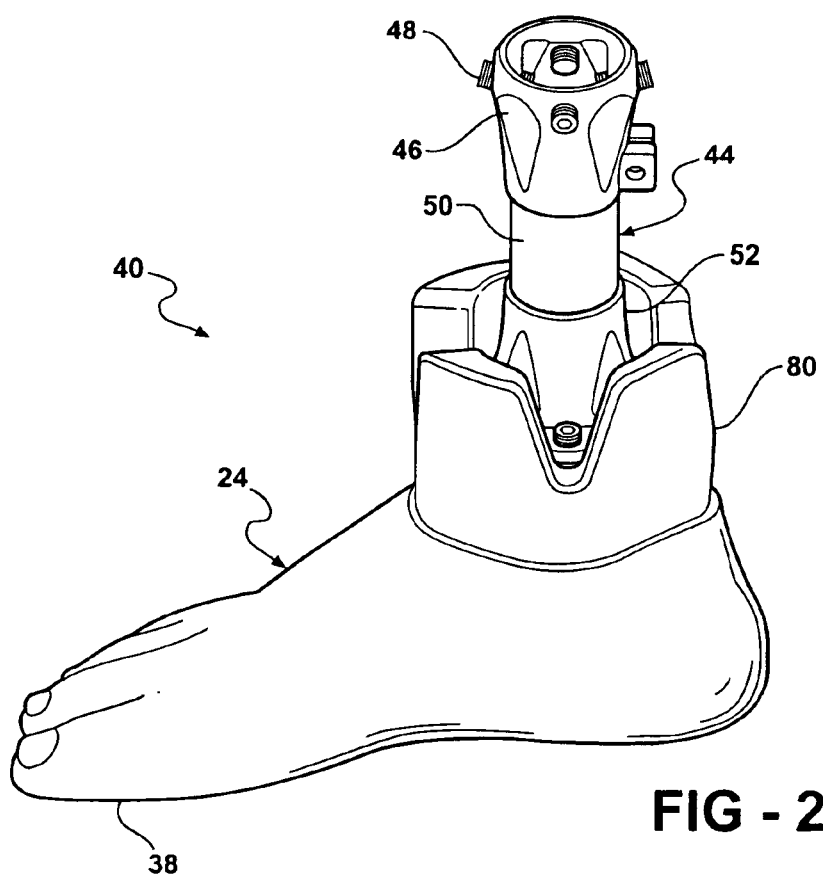
FIG. 2 is a perspective view of a prosthetic foot with an ankle block attached thereto and the temporary endoskeletal pylon.
Figure 3:
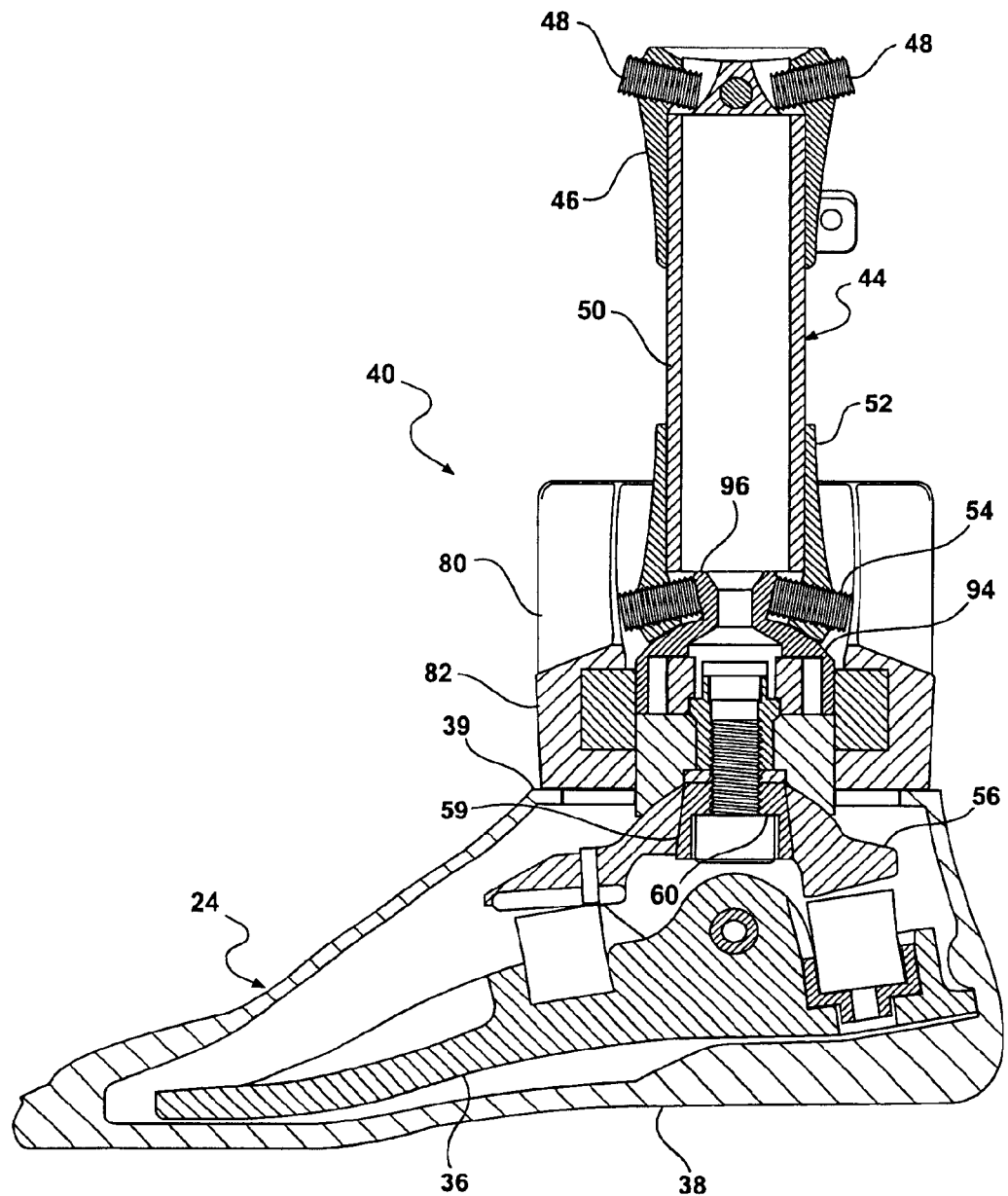
FIG. 3 is a cross-section of the prosthetic foot and temporary endoskeletal pylon of FIG. 2.

For purposes of description herein, the terms "upper", "lower", "left", "rear", "right", "front", "vertical", "horizontal", and derivatives thereof shall relate to the invention as oriented in FIG. 2-3. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
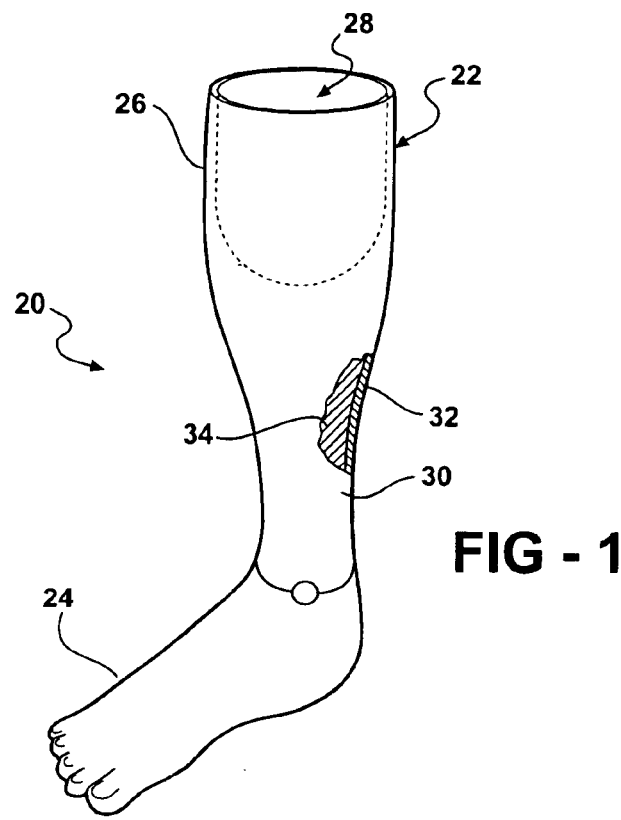
FIG. 1 is a perspective view of an exoskeletal leg prosthesis embodying the present invention.

Turning to the drawings, FIG. 1 shows an exoskeletal prosthetic leg 20 which is one of the preferred embodiments of the present invention and illustrates its various components. Exoskeletal leg prosthesis 20 includes a leg portion 22 having at an upper portion thereof a leg socket 26 defining a cavity 28 for receiving the leg of a user. The socket 26 is supported by leg support 30. Leg support 30 is constructed of a structural foam core 34 and further wherein socket 26 and structural foam core 34 are encased in a shell 32. Shell 32 is typically constructed of a fiber-reinforced resin, or more commonly known as a composite shell, the lay up and construction of which is well known in the art. A foot portion 24 is attached to the bottom of leg portion 22.

Figure 4:
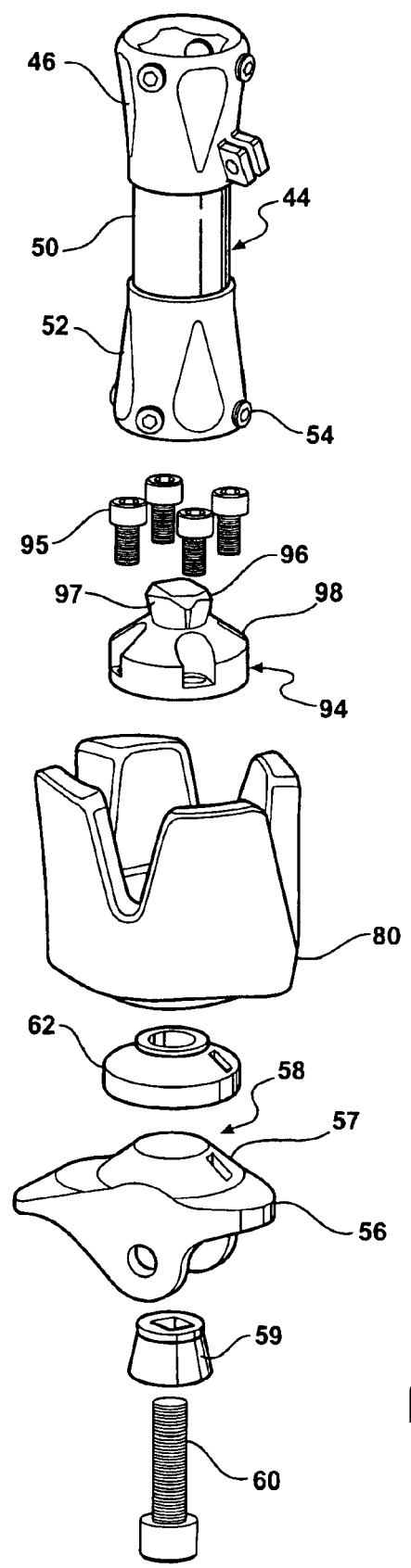
FIG. 4 is an exploded view of the attachment of the prosthetic foot ankle to the temporary endoskeletal pylon.

Turning now to FIGS. 2-4, a temporary leg assembly 40 is shown wherein foot portion 24 covered by foot shell 38 has an ankle block 80 attached thereto. A temporary endoskeletal pylon 44 is affixed to ankle block 80. Temporary endoskeletal pylon 44 comprises an endoskeletal tube 50 having a tube adapter 52 affixed at a bottom thereof and a socket adapter 46 affixed at a top thereof. Socket adapter 46 is temporarily affixed to socket 26 in a manner that is well known in the art whereby socket 26 has a pyramid portion 27 (FIG. 9B) affixed to a bottom thereof which is received in socket adapter 46 and retained in place by set screws 48 bearing upon individual faces of the pyramid. In this manner, temporary endoskeletal pylon 44 can be retained and adjusted with respect to socket 26 by adjusting set screws 48.

FIG. 3 discloses a prosthetic foot 36 and attached ankle 56. The construction of foot 36 and ankle 56 is similar to the construction of the prosthetic foot assembly disclosed in U.S. Pat. No. 6,129,766, which is hereby incorporated by reference. Further description of the foot 36 and interface with ankle 56 is not discussed herein. Foot 36 and ankle 56 are received in cosmetic foot shell 38 to provide the aesthetic appearance of a human foot. Foot shell 38 has an upper surface 39, which generally defines an opening through which the foot 36 and ankle 56 are received. Ankle 56 differs from the ankle in U.S. Pat. No. 6,129,766 in that ankle 56 includes a spherical top attachment surface and a tapered attachment hole 58 centrally located therein. Tapered bolt insert 59 is received in attachment hole 58 such that the narrow portion of the tapered insert 59 is oriented toward the top. A foot bolt 60 is inserted through tapered insert 59 and ankle 56 from the bottom such that the threads of bolt 60 extend upwardly through ankle 56 and insert 59.

Figure 5:
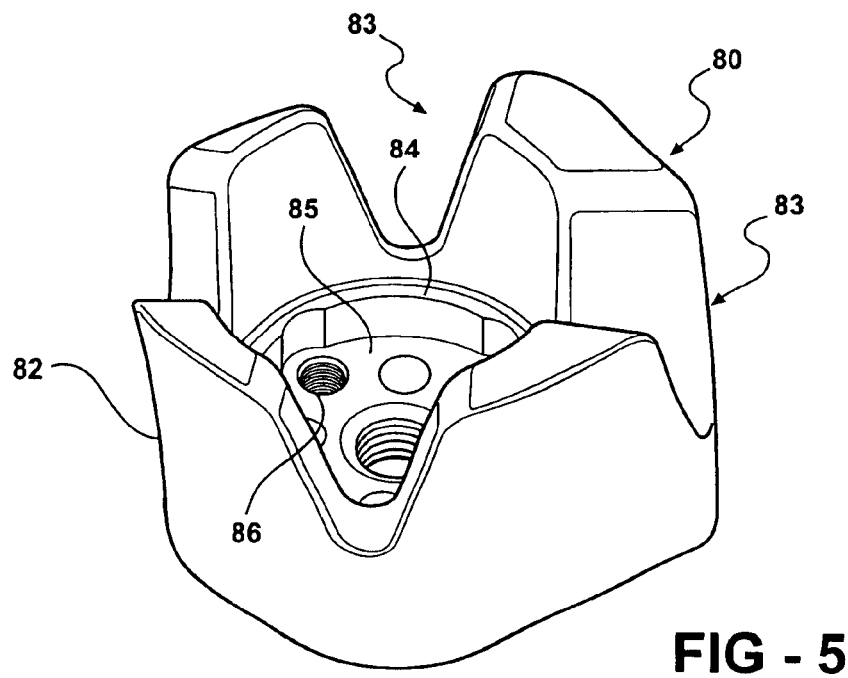
FIG. 5 is a perspective view of an ankle block.
Figure 6:
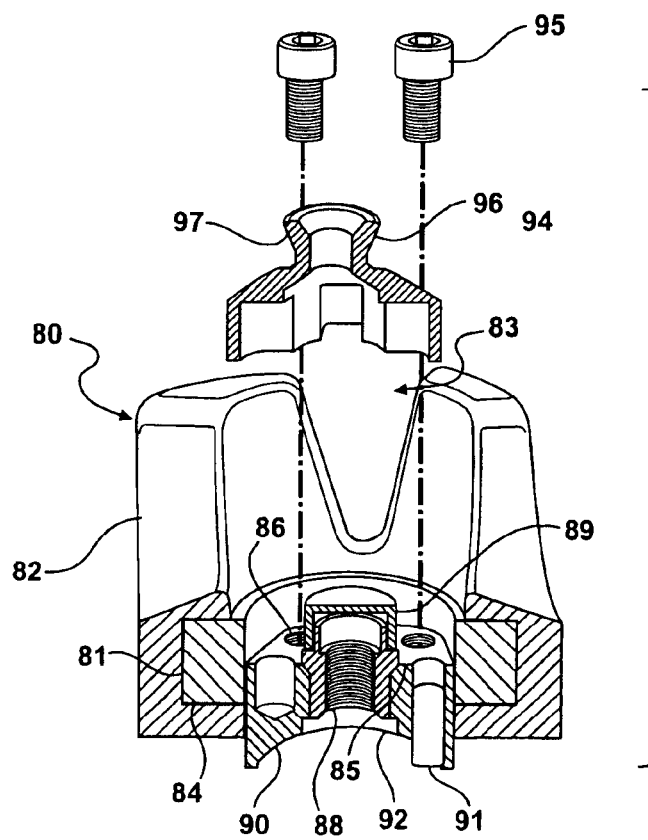
FIG. 6 is a cross-section of the ankle block of FIG. 5 and the pyramid adapter tool.

An ankle block 80 as shown in FIGS. 5-6 is attached to ankle 56 with foot bolt 60. Referring now to FIGS. 5-6, ankle block 80 comprises an insert 84 which is typically a machined aluminum structure since a major objective of prosthetic construction is to minimize the weight thereof. Insert 84 includes a machined mounting surface 85, which includes four threaded holes 86 circumferentially spaced therearound. Insert 84 further defines a central hole into which is received a threaded insert 88. Threaded insert 88 can be made from steel or titanium or other sturdy metal for receiving the threaded end of foot bolt 60. The bottom interface surface 90 of insert 84 is spherically concave, the radius of which mates with the spherical radius of the upper surface 57 of ankle 56. A circular recess 92 is formed in the top of spherical interface surface 90 and an alignment pin 91 is interferingly received in a hole in insert 84 such that one end of pin 91 extends into the recess defined by spherical interface surface 90. The portion of pin 91 that extends into spherical recess 90 is received in a like placed recess of spherical mounting surface 57 on ankle 56 to ensure a desired rotational alignment between ankle block 80 and ankle 56. A cap 89 is affixed over a top end of threaded insert 88 to seal the space above insert 84 from the threaded hole in insert 88. A urethane overmold 82 is molded around body 81 of insert 84. Urethane overmold 82 is rigid and extends upwardly from insert 84 to form a cup like structure thereby defining a central recess. Notches 83 are formed in over mold 82 for access as to the central recess for the purpose described below. As seen in FIG. 3, the exterior contour of over mold 82 is slightly smaller than the outer perimeter of upper surface 39 of foot shell 38. As the final prosthesis is an exoskeletal prosthesis, the slightly smaller periphery of urethane over mold 82 from that of upper surface 39 accommodates the thickness of the composite shell 32 to be formed later, thus providing a smooth transition from foot shell 38 to the exterior surface of composite shell 32.

Referring to FIGS. 4 and 6, a pyramid adapter tool 94 is placed on mounting surface 85 of ankle block 80 and is fastened thereto with four cap screws threaded into threaded holes 86 of insert 84. Pyramid adapter tool 94 has at a top thereof a pyramid 96 with a plurality of pyramid faces 97 therearound, which in the present embodiment comprises four pyramid faces. Pyramid adapter tool 94 has a spherical upper surface 98 from which pyramid 96 extends at a top center of tool 94.

As seen in FIGS. 3 and 4, endoskeletal leg 44 is affixed to pyramid adapter tool 94 wherein tube adapter 52 is received over pyramid 96 and set screws 54 are threaded to bear against pyramid faces 97. One setscrew 54 is aligned with each face of pyramid 96. This method of attaching leg 44 to pyramid 96 is the same as the attachment of socket adapter 46 to the pyramid affixed to leg socket 26.

In use, and as illustrated in FIGS. 9A-J, the prosthetist will, through his experience and expertise, work with the wearer of prosthetic leg 20 in a dynamic manner to adjust foot portion 24 with respect to socket 26 to provide the optimum alignment of foot portion 24 with respect to socket 26. The alignment is accomplished by repeated adjustments of set screws 48 to adjust endoskeletal pylon 44 with respect to socket 26 and by adjusting set screws 54 in tube adapter 52 to adjust foot portion 24, including ankle block 80, with respect to endoskeletal pylon 44 and socket 26. Notches 83 formed in the upper portion of urethane molding 82 facilitate the necessary access to set screws 54.

Once the foot portion 24 has been optimally aligned with leg socket 26 (FIGS. 9C–D), the prosthesis is removed from the user's leg and inserted into a fixture (FIG. 9E). Fixtures for holding leg prostheses for adjustment and work thereon are well known in the art, and thus specific details are not illustrated herein. The prosthesis is clamped into the fixture 18 such that both foot portion 24 and leg socket 26 are individually affixed to the fixture. Once the leg socket 26 and foot 24 are retained in their adjusted relationship, endoskeletal pylon 44 is removed from between leg socket 26 and ankle block 80 (FIG. 9F). Once endoskeletal pylon 44 has been removed, cap screws 95 are removed from pyramid adapter tool 94 and pyramid adapter tool 94 is removed from ankle block 80. Once the pylon 44 and tool 94 have been removed, a flexible plastic sleeve 100 such as a plastic bag is affixed to a lower portion of leg socket 26 and to the exterior surface of urethane over mold 82 of ankle block 80. An expanding structural foam 102 is then placed in the bag and allowed to expand and cure. Once the foam has cured, the plastic bag can be removed and the foam core extending from the leg socket 26 to ankle block 80 can be trimmed and shaped to a desired configuration and in a manner known in the art (FIG. 9I). After the structural foam core has been shaped, either in the shape of a human leg or some other desired shape, the fiber reinforced shell 32 is constructed to extend from the upper surface 39 of foot shell 38 to the top opening of cavity 28 in leg socket 26. The construction of the fiber reinforced shell 32 can be accomplished in any of a number of known methods depending upon the type of fiber reinforcement and curable resins utilized to fabricate the shell 32. Once the shell has cured, the leg prosthesis 20 is ready for use by the wearer whereby foot portion 24 is reattached (FIG. 9J) and is optimally aligned with leg socket 26 with a lightweight composite type construction therebetween and not relying on multiple mechanical interfaces that have the potential to become misaligned, loose, or create undesirable noise.

Figure 8:
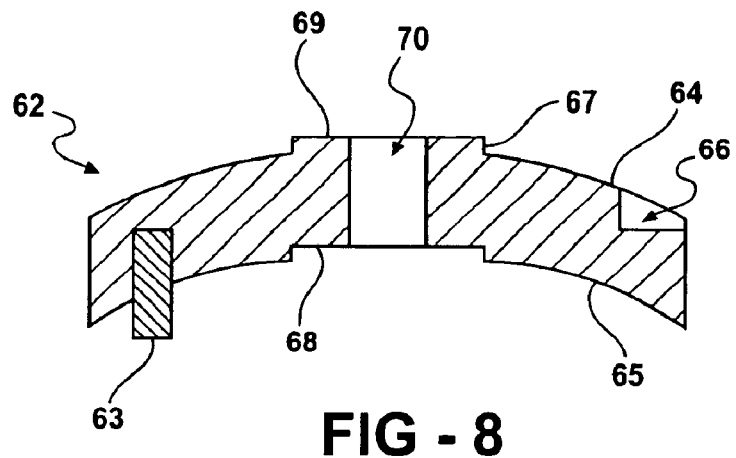
FIG. 8 is a cross-section of a spacer.

When a leg prosthesis such as prosthesis 20 is fabricated for a child, it is also desirable to accommodate for the child's growth without requiring the complete construction of a new prosthesis for every growth increment of the child. To facilitate the growth adjustment for a child, a spacer 62 as shown in FIG. 8 is provided. Spacer 62 comprises a body 69 which has a spherical upper surface 64 and a like spherical bottom surface 65 wherein spherical surfaces 64 and 65 have the same radius as spherical mounting surface 57 on ankle 56 and concave spherical interface surface 90 in ankle block 80. Spacer 62 includes a raised circular boss 67 in axial alignment with a vertical hole 70 through a center of spacer 62. Bottom surface 65 also includes an axially centered circular recess 68 slightly larger in diameter than raised boss 67. Upper surface 64 also defines a recess 66 proximate to an outer periphery of spacer 62. An alignment pin 63 extends from bottom surface 65 and is positioned 180 degrees opposite from recess 66.

Figure 7:
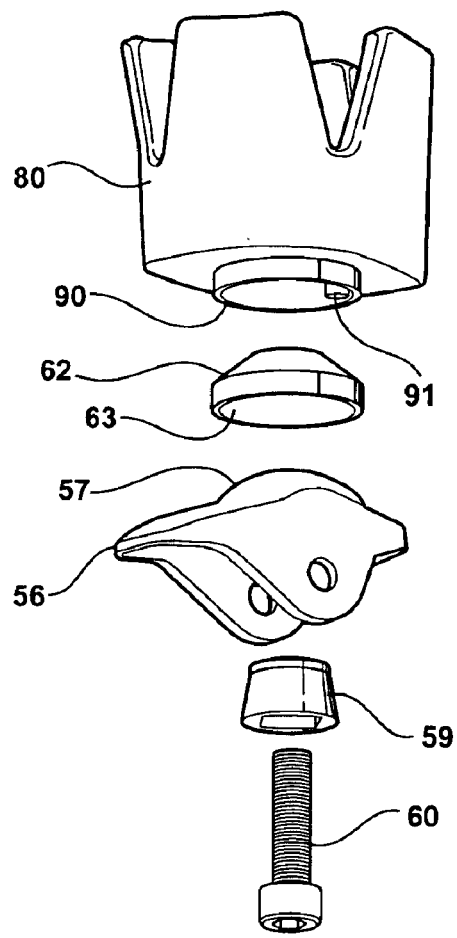
FIG. 7 is bottom perspective view of the attachment of the ankle to the ankle block.

As illustrated in FIG. 7, when the prosthesis needs to be compensated for a child's growth, foot 36 is removed from ankle 56 and foot bolt 60 is removed, thus disassembling ankle 56 from ankle block 80. Spacer 62 is placed in concave recess 90 of ankle block 80 such that alignment pin 91 is received in alignment recess 66 of spacer 62 and ankle 56 is then mated to the bottom of spacer 62. Boss 67 of spacer 62 is received in circular recess 92 of ankle block 80 to assure axial alignment of spacer 62 with ankle block 80 and alignment pin 63 is received in a corresponding alignment recess in ankle 56. A longer foot bolt 60 is then inserted from the bottom of ankle 56 and threaded into ankle block 80 whereupon foot 36 is again reattached to ankle 56. Spacer 62 is typically 0.250 inches in thickness, and up to two spacers can be utilized between ankle block 80 and ankle 56, thus providing for ½ inch of growth accommodation for a child wearing the prosthesis.

In the foregoing description those skilled in the art will readily appreciate that modifications may be made to the invention without departing from the concepts disclosed herein. Such modifications are to be considered as included in the following claims, unless these claims expressly state otherwise.

What is claimed is:

1. A method of constructing an exoskeletal leg prosthesis, said method comprising the steps:

forming a leg socket in an upper end of a leg portion for receiving the leg of a user therein;

affixing a first temporary adapter to a bottom of the leg portion attaching an ankle block to the top of a prosthetic foot, the ankle block including an insert for attaching the block to the foot and an outermold molded over the insert and having an upwardly extending portion defining a recess therein;

affixing a second temporary adapter to the insert of the ankle block;

attaching an endoskeletal pylon system to the adapters on the ankle block and leg portion to create a temporary adjustable prosthetic leg; adjusting the endoskeletal pylon to align the prosthetic foot with the leg portion, removing the prosthetic foot from the ankle block;

retaining the adjusted leg portion and the ankle block in a fixed alignment relative to one another;

removing the endoskeletal pylon and temporary adapters while maintaining the fixed adjusted alignment between the leg portion and the ankle block;

molding a structural foam support between the leg portion and the ankle block; and reattaching the prosthetic foot.

2. A method for constructing an exoskeletal prosthetic leg, said method comprising the steps:

providing a leg portion defining a socket;

attaching an ankle block to a prosthetic foot by an insert in the ankle block;

attaching a temporary adjustable endoskeletal pylon between the leg portion and the insert of the ankle block;

adjusting the pylon to dynamically align the prosthetic foot with respect to the leg portion;

removing the temporary endoskeletal pylon while maintaining the adjusted alignment of the leg portion with respect to the insert of the ankle block; and removing the foot from the ankle block; and constructing an inner foam core between the leg portion and the ankle block and insert; and reattaching the foot to the ankle block; and applying a laminated shell to an exterior of the leg socket, the foam core, and the ankle block.

* * * * *